US012008695B2

(12) United States Patent
Kaushik et al.

(10) Patent No.: US 12,008,695 B2
(45) Date of Patent: Jun. 11, 2024

(54) METHODS AND SYSTEMS FOR TRANSLATING MAGNETIC RESONANCE IMAGES TO PSEUDO COMPUTED TOMOGRAPHY IMAGES

(71) Applicant: GE Precision Healthcare LLC, Milwaukee, WI (US)

(72) Inventors: Sandeep Kaushik, Bangalore (IN); Dattesh Shanbhag, Bangalore (IN); Cristina Cozzini, Bavaria (DE); Florian Wiesinger, Bavaria (DE)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 585 days.

(21) Appl. No.: 17/033,183

(22) Filed: Sep. 25, 2020

(65) Prior Publication Data
US 2022/0101576 A1 Mar. 31, 2022

(51) Int. Cl.
*G06T 11/60* (2006.01)
*A61B 5/00* (2006.01)
*A61B 5/055* (2006.01)
*G01R 33/56* (2006.01)
*G06F 18/214* (2023.01)

(52) U.S. Cl.
CPC ............ *G06T 11/60* (2013.01); *A61B 5/0033* (2013.01); *A61B 5/055* (2013.01); *A61B 5/7267* (2013.01); *G01R 33/5608* (2013.01); *G06F 18/214* (2023.01); *G06T 2210/41* (2013.01); *G06V 2201/033* (2022.01)

(58) Field of Classification Search
CPC .................. A61B 5/055; A61B 5/7267; G06T 2207/10088; G06V 10/82; G01R 33/5608
See application file for complete search history.

(56) References Cited

U.S. PATENT DOCUMENTS

2017/0100078 A1* 4/2017 Han .................... A61N 5/1039

OTHER PUBLICATIONS

Liu, Fang, et al. "Deep learning MR imaging-based attenuation correction for PET/MR imaging." Radiology 286.2 (2018): 676-684. (Year: 2018).*
Gupta, Dinank, et al. "Generation of synthetic CT images from MRI for treatment planning and patient positioning using a 3-channel U-net trained on sagittal images." Frontiers in oncology 9 (2019): 964. (Year: 2019).*
Kaushik, S. et al., "MRI to CT Translation using Multitask Network with Focused Region of Interest Accuracy," Proceedings of the 23rd International Conference on Medical Image Computing and Computer Assisted Intervention (MICCAI 2020), Oct. 4, 2020, Lima, Peru, 10 pages.

* cited by examiner

*Primary Examiner* — Vincent Rudolph
*Assistant Examiner* — Raphael Schwartz
(74) *Attorney, Agent, or Firm* — McCoy Russell LLP

(57) ABSTRACT

Various methods and systems are provided for translating magnetic resonance (MR) images to pseudo computed tomography (CT) images. In one embodiment, a method comprises acquiring an MR image, generating, with a multi-task neural network, a pseudo CT image corresponding to the MR image, and outputting the MR image and the pseudo CT image. In this way, the benefits of CT imaging with respect to accurate density information, especially in sparse regions of bone which exhibit with high dynamic range, may be obtained in an MR-only workflow, thereby achieving the benefits of enhanced soft-tissue contrast in MR images while eliminating CT dose exposure for a patient.

15 Claims, 9 Drawing Sheets

METHODS AND SYSTEMS FOR TRANSLATING MAGNETIC RESONANCE IMAGES TO PSEUDO COMPUTED TOMOGRAPHY IMAGES

FIELD

Embodiments of the subject matter disclosed herein relate to magnetic resonance imaging, and more particularly, to translating magnetic resonance images to computed tomography-like images.

BACKGROUND

The electron density information in the body is essential for accurate dose calculation in radiation therapy treatment planning and to compute attenuation correction maps in positron emission tomography (PET) imaging. In traditional radiation therapy treatment planning and in PET imaging, a computed tomography (CT) image provides the necessary information of electron density and attenuation characteristics of tissue. In particular, CT imaging enables the accurate depiction of internal anatomical structures, such as bone, soft tissue, and blood vessels, at the same time.

BRIEF DESCRIPTION

In one embodiment, a method comprises acquiring a magnetic resonance (MR) image, generating, with a multi-task neural network, a pseudo CT image corresponding to the MR image, and outputting the MR image and the pseudo CT image. In this way, the benefits of CT imaging with regard to accurate density information, especially in sparse regions of bone which exhibit with high dynamic range, may be obtained in an MR-only workflow, thereby achieving the benefits of enhanced soft-tissue contrast in MR images while eliminating CT dose exposure for a patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 3:
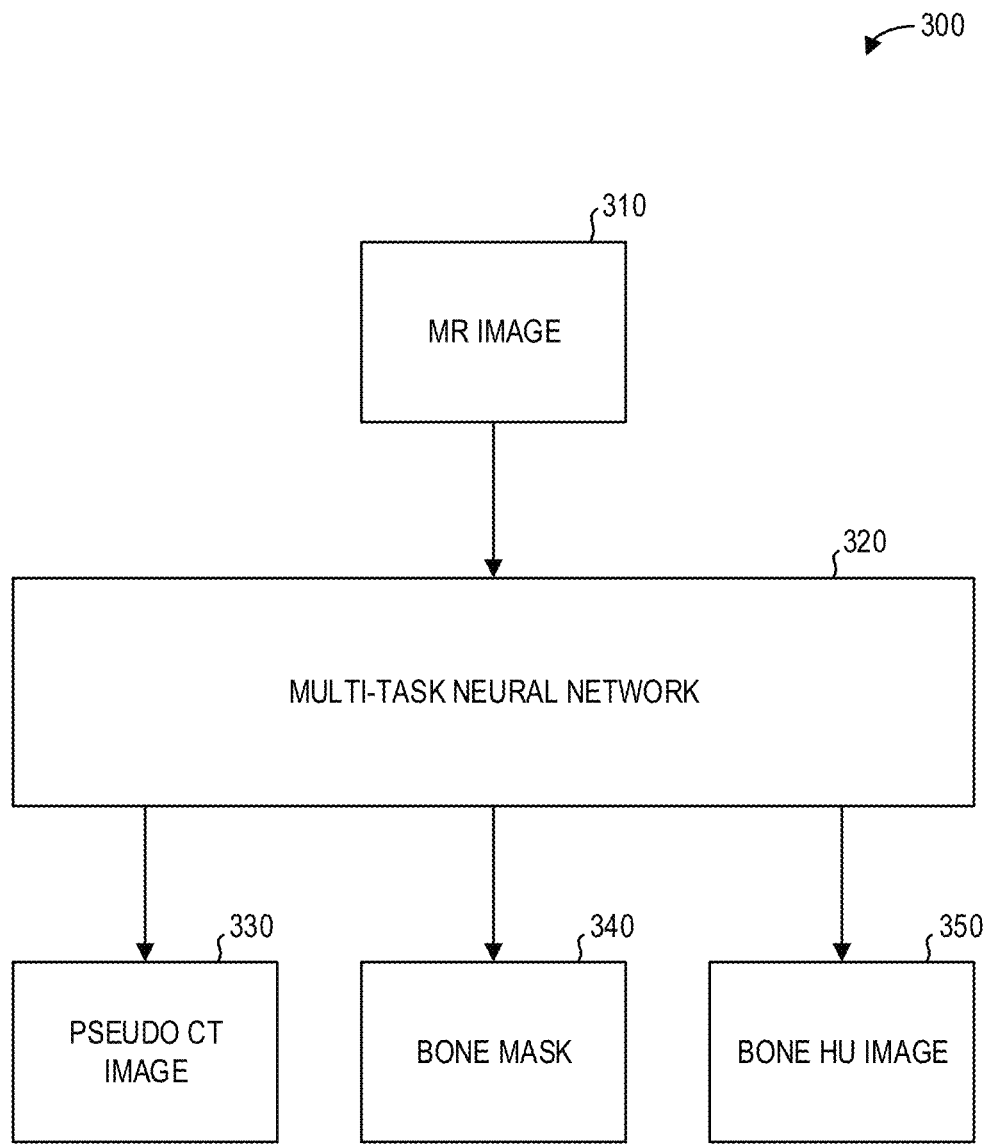
FIG. 3 is a schematic diagram illustrating a layout of an embodiment of a multi-task neural network for transforming an MR image to a pseudo CT image, according to an embodiment of the disclosure.
Figure 4:
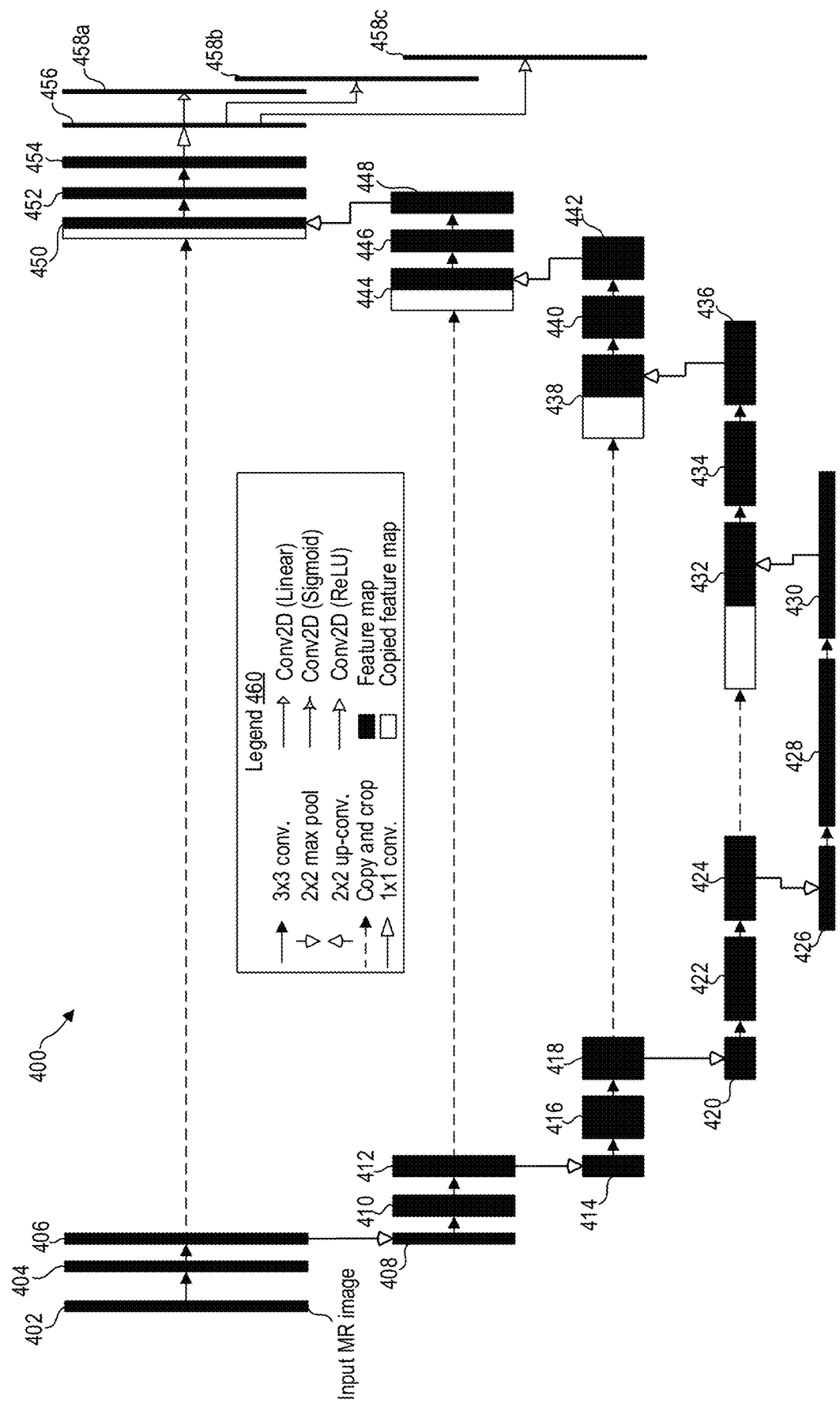
FIG. 4 is a schematic diagram illustrating a layout of a deep multi-task neural network which can be used in the image processing system of FIG. 2, according to an embodiment of the disclosure.

The following description relates to various embodiments for translating an MR image to a pseudo CT or a CT-like image. The electron density information in the body is essential for accurate dose calculation in radiation therapy (RT) treatment planning and to compute attenuation correction maps in positron emission tomography (PET) imaging. In traditional RT treatment planning and in PET/CT imaging, a CT image provides the necessary information of electron density and attenuation characteristics of tissues. However, there is a growing trend of using MR-only clinical workflows to leverage the benefits of enhanced soft-tissue contrast in MR images. In order to replace a CT image, the density map for RT dose calculation and PET/MR attenuation correction needs to be inferred from MM. One approach to replacing CT with MRI may include mapping an MR image to a corresponding CT image to provide CT-like Hounsfield unit (HU) values as a pseudo CT (pCT) image. In this way, certain benefits of CT imaging may be obtained using only an MRI system, such as the MR apparatus depicted in FIG. 1. However, bone values may range from 250 HU to over 2000 HU in a CT image, while only occupying a fraction of a region of a body. As such, previous approaches to generating pCT images based on machine learning models, for example, tend to train biased towards the spatially dominant values from soft tissue and background regions, due to the large dynamic range and spatial sparsity of bone regions, thereby resulting in reduced accuracy within bone regions. Moreover, bone regions become sparser at higher densities and contribute even less towards network optimization. Inaccurate bone value assignment in pseudo CT images could result in a range of errors in dose calculation for RT treatment planning, for example. In order to better utilize MM for RT treatment planning, an image processing system, such as the image processing system depicted in FIG. 2, may include a deep multi-task neural network module configured to generate pCT images with accurate bone value assignment. In particular, the deep multi-task neural network module takes an MR image as input and outputs a pCT image with accurate HU value assignments across different densities and tissue classes. In one example, in order to increase the accuracy of bone estimation for synthesized CT, a multi-task neural network is assigned tasks of whole image translation, accurate segmentation of a region of interest, and image value estimation within the region of interest. For example, as depicted in FIG. 3, the multi-task neural network thus outputs a pseudo CT image, a bone mask, and a bone HU image or bone density map for the three respective tasks. The multi-task neural network may be implemented as a two-dimensional U-Net convolutional neural network, for example as depicted in FIG. 4, with multiple output layers. The multi-task neural network may be trained, for example according to a training method such as the method depicted in FIG. 5, to perform the multiple tasks simultaneously, such that the related tasks improve generalization of the network. A method for implementing such a multi-task neural network after training, such as the method depicted in FIG. 6, may include generating a pseudo CT image from an MR image and updating the pseudo CT image with the bone HU image also generated by the multi-task neural network. By constructing a neural network as described herein and training the neural network to perform multiple correlated tasks, the accuracy of pCT generation relative to other approaches, even other deep neural network-based approaches, is improved, as depicted by qualitative and quantitative comparisons in FIGS. 7-9.

Figure 1:
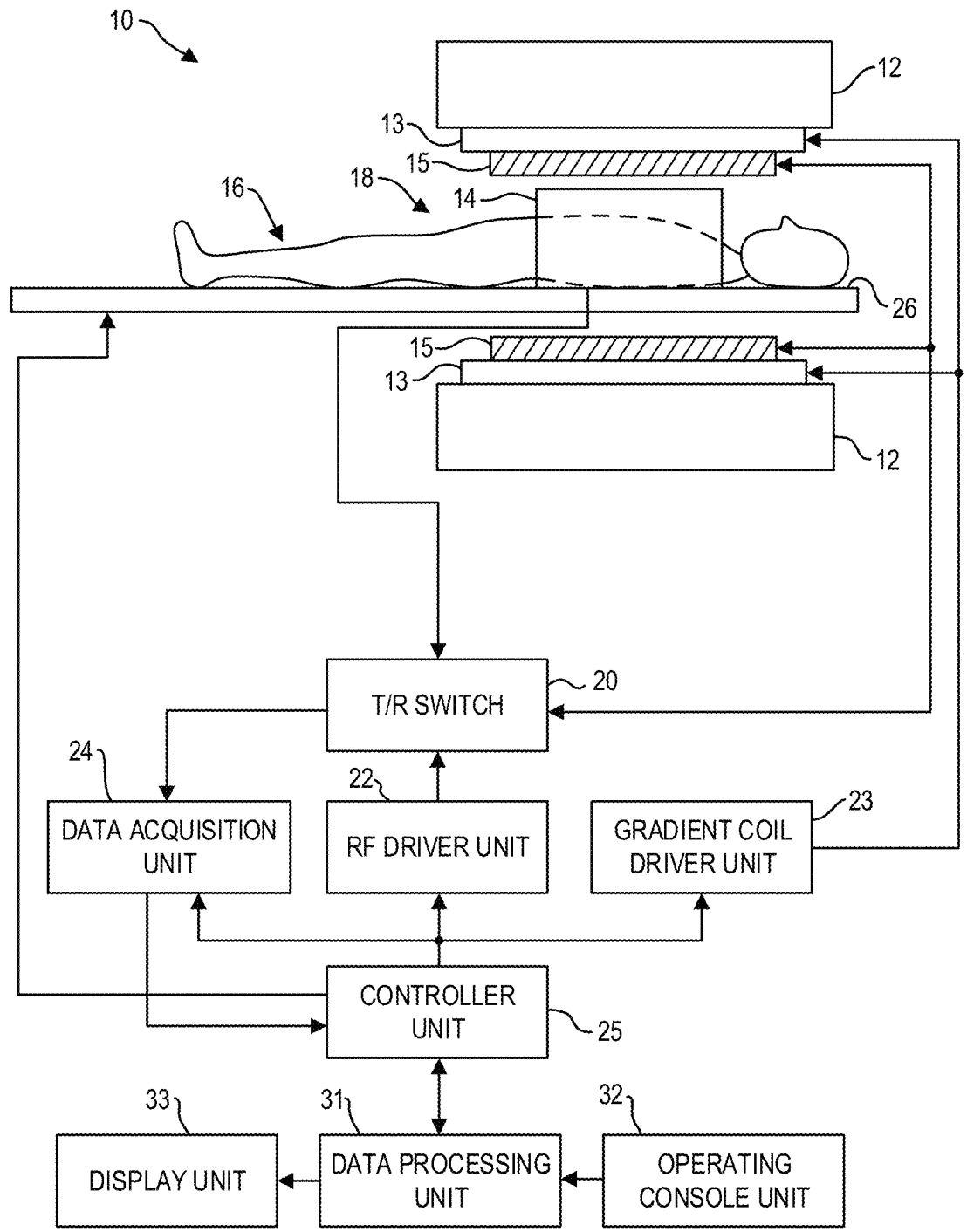
FIG. 1 is a block diagram of an MM system according to an embodiment of the disclosure.

Turning now to the figures, FIG. 1 illustrates a magnetic resonance imaging (MRI) apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MM apparatus 10 also includes a gradient coil unit 13 that forms a gradient magnetic field in the imaging space 18 so as to provide the magnetic resonance signals received by the RF coil arrays (e.g., RF coil unit 14 and/or RF body coil unit 15) with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MM apparatus 10 and replaced with another RF coil unit, the RF body coil unit 15 is fixedly attached and connected to the MM apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

Figure 2:
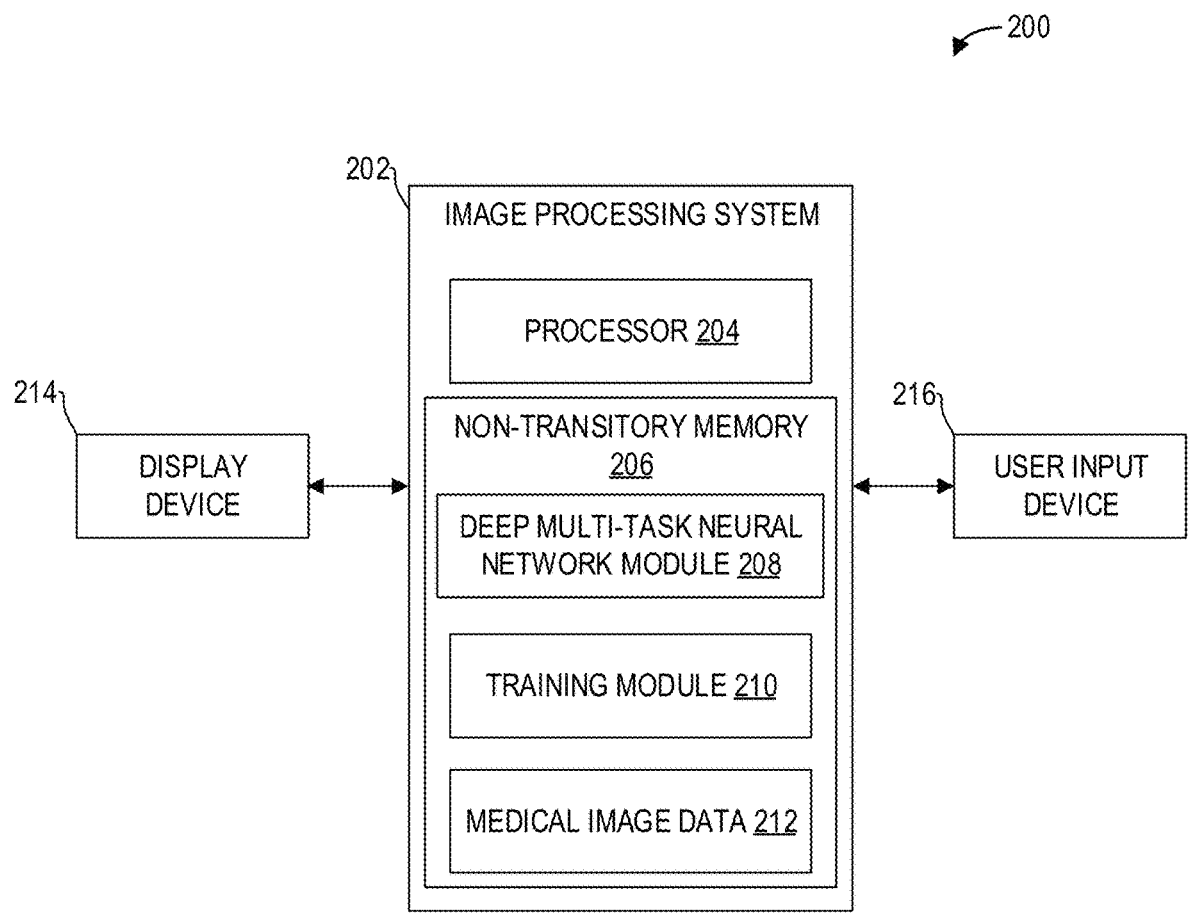
FIG. 2 is a schematic diagram illustrating an image processing system for transforming an MR image to a pseudo CT image using a deep multi-task neural network, according to an embodiment of the disclosure.

Referring to FIG. 2, a medical image processing system 200 is shown, in accordance with an exemplary embodiment. In some embodiments, the medical image processing system 200 is incorporated into a medical imaging system, for example, an MRI system, CT system, X-ray system, PET system, ultrasound system, and so on. In some embodiments, the medical image processing system 200 is disposed at a device (e.g., edge device, server, etc.) communicably coupled to the medical imaging system via wired and/or wireless connections. In some embodiments, the medical image processing system 200 is disposed at a separate device (e.g., a workstation) which can receive images from the medical imaging system or from a storage device which stores the images generated by the medical imaging system. The medical image processing system 200 may comprise image processing system 202, user input device 216, and display device 214.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep multi-task neural network module 208, training module 210, and medical image data 212 such as magnetic resonance image data. Deep multi-task neural network module 208 may include one or more deep multi-task neural networks, comprising a plurality of parameters (including weights, biases, activation functions), and instructions for implementing the one or more deep multi-task neural networks to receive MR images and map the MR image(s) to output, wherein a pseudo CT image corresponding to the MR image may be produced from the output. For example, deep multi-task neural network module 208 may store instructions for implementing a multi-task neural network, such as the multi-task convolutional neural network (CNN) of CNN architecture 400, shown in FIG. 4. Deep neural network module 208 may include trained and/or untrained multi-task neural networks and may further include various data, or metadata pertaining to the one or more multi-task neural networks stored therein.

Non-transitory memory 206 may further store training module 210, which comprises instructions for training one or more of the deep neural networks stored in deep multi-task neural network module 208. Training module 210 may include instructions that, when executed by processor 204, cause image processing system 202 to conduct one or more of the steps of method 500, discussed in more detail below. In some embodiments, training module 210 includes instructions for implementing one or more gradient descent algorithms, applying one or more loss functions for each task and a composite loss function based on the one or more loss functions for each task, and/or training routines, for use in adjusting parameters of one or more deep multi-task neural networks of deep multi-task neural network module 208. In some embodiments, training module 210 includes instructions for intelligently selecting training data sets from medical image data 212. In some embodiments, training data sets comprise corresponding pairs of MR and CT medical images of a same anatomical region for a same patient. Further, in some embodiments, training module 210 includes instructions for generating training data sets by generating, based on CT images in the medical image data 212, a bone mask and a bone HU image. In some embodiments, the training module 210 is not disposed at the image processing system 202. The deep multi-task neural network module 208 includes trained and validated network(s).

Non-transitory memory 206 further stores medical image data 212. Medical image data 212 includes for example, MR images captured from an MRI system, CT images acquired by a CT imaging system, and so on. For example, the medical image data 212 may store corresponding MR and CT images of patients. In some embodiments, medical image data 212 may include a plurality of training data pairs comprising pairs of MR images and CT images.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

Image processing system 200 may further include user input device 216. User input device 216 may comprise one or more of a touchscreen, a keyboard, a mouse, a trackpad, a motion sensing camera, or other device configured to enable a user to interact with and manipulate data within image processing system 202. As an example, user input device 216 may enable a user to make a selection of a medical image, such as an MR image, to transform to a pseudo CT image.

Display device 214 may include one or more display devices utilizing virtually any type of technology. In some embodiments, display device 214 may comprise a computer monitor, and may display unprocessed and processed MR images and/or pseudo CT images. Display device 214 may be combined with processor 204, non-transitory memory 206, and/or user input device 216 in a shared enclosure, or may be peripheral display devices and may comprise a monitor, touchscreen, projector, or other display device known in the art, which may enable a user to view medical images, and/or interact with various data stored in non-transitory memory 206.

It should be understood that image processing system 200 shown in FIG. 2 is for illustration, not for limitation. Another appropriate image processing system may include more, fewer, or different components.

Turning to FIG. 3, a schematic of a first embodiment of a translation process 300 for translating an MR image 310 to a pseudo CT or pCT image 330 is shown. In particular, the translation process 300 includes inputting an MR image 310 to a multi-task neural network 320, which in turn outputs a pseudo CT image 330, a bone mask 340, and a bone HU image 350 corresponding to the input MR image 310.

The multi-task neural network 320 thus maps the MR image 310 to its corresponding pseudo CT image 330 which matches a ground truth CT image (not shown). A CT image ($I_{CT}$) may be considered as a spatially non-overlapping set of three distinct density classes:

$$I_{CT} = (I_{air} \cup I_{tissue} \cup I_{bone}),$$

where $I_{air}$ corresponds to air, $I_{tissue}$ corresponds to tissue, and $I_{bone}$ corresponds to bone. With the assumption that an MR image $I_{MR}$ (e.g., MR image 310) and the CT image $I_{CT}$ are spatially aligned, thereby implying the spatial alignment of a pseudo CT image $I_{pCT}$ (e.g., pseudo CT image 330), the error between the CT image and the pCT image 330 may be defined as $$e = I_{CT} - I_{pCT}.$$

Smaller values of e result in density deviation within a class. However, a larger value of e results in a pixel being classified differently; such an error is more likely to occur at a boundary location between two classes and could lead to a cumulative classification error. Thus, the error e may be seen to comprise both a classification error between different classes and image value estimation error within each class. The overall objective of the network is to map the MR image 310 to the pCT image 330 by minimizing the error e between the ground truth CT image and the pCT image 330.

Rather than configure a neural network with a single task of mapping the MR image 310 to the pCT image 330, the multi-task neural network 320 is configured with a plurality of tasks such that the tasks of classification and regression are separated. By separating the tasks of classification and regression, and by optimizing the multi-task neural network 320 to simultaneously reduce both errors, implicit reinforcement can be achieved towards each of the correlated tasks. Although the tasks are correlated, the multi-task neural network 320 is expected to learn them differently from one another, and in order to optimize the tasks individually, each task is driven by a dedicated loss function. As described further herein, the multi-task neural network 320 is configured with three tasks: whole image translation, accurate segmentation of a region of interest, and image value estimation within the region of interest. Each task is driven by a loss function which is tailored to minimize a specific error, thus contributing to the overall optimal state of the multi-task neural network 320.

Mean absolute error (MAE) is a suitable loss function for image regression. However, MAE is a global measure which does not account for imbalance between regional volumes of each class in the image, nor does MAE able to focus on a region of the image as needed. MAE may be adapted to include the ability of spatial focus by weighting the loss of a region positively compared to the rest of the image, where the relative volume of a region may be used as an implicit weight factor. For example, for a given region k with $N_k$ samples, the mean absolute error (MAE) within the region k is calculated as:

$$MAE_k = \frac{1}{N_k} \sum_{i=1}^{N_k} |y_i - \hat{y}_i|,$$

where $y_i$ is the true value and $\hat{y}_i$ is the estimated value. The weighted MAE for an image with two complementary spatial classes {k, k'} including a first class k and a second class k' can then be defined as:

$$wMAE_k = \frac{N_{k'}}{N} * MAE_k + \frac{N_k}{N} * MAE_{k'}, \text{ where}$$

$$N_k + N_{k'} = N$$

is the volume of the entire image. In a scenario of class imbalance where the volume $N_k$ of the first class is much smaller than the volume $N_{k'}$ of the second class, the value of the mean absolute error $MAE_k$ for the first class is emphasized by the volume $N_{k'}$ of the second class, such that the mean absolute error $MAE_k$ of the first class comparable to the mean absolute error $MAE_{k'}$ of the second class. This result can be seen as spatial focus on a region within the image which is represented by the first class k. When the volume $N_k$ of the first class equals the volume $N_{k'}$ of the second class, for example such that each volume equals half of the total volume N of the image, then the weighted mean absolute error (e.g., $wMAE_k$) described above becomes the global mean absolute error MAE.

For the segmentation task, a smoothed Dice coefficient loss is often the preferred loss function. Between a given pair of segmentation probability maps, the Dice loss is defined as:

$$L_D = 1 - \left(2\sum_{i=1}^{N} x_i \hat{x}_i\right) \bigg/ \left(\sum_{i=1}^{N} x_i^2 + \sum_{i=1}^{N} \hat{x}_i^2\right),$$

where $x_i$ and $\hat{x}_i$ are the true and predicted bone probability values, respectively, in the image.

As mentioned hereinabove, the multi-task neural network 320 is configured to learn a plurality of tasks with the primary aim of generating a pseudo CT image 330. The tasks include a first task of generating a pseudo CT image 330, a second task of generating a bone mask 340, and a third task of generating a bone HU image 350 (e.g., the image values within the bone region of interest in terms of HU). To generate a pseudo CT image $I_{pCT}$, the primary task of the multi-task neural network 320 is the whole image regression of the entire CT value (HU) range corresponding to different classes. This first task or the pCT image task is thus driven by the regression loss for the body region:

$$L_{body}^{reg} = MAE_{body}.$$

To generate a bone mask $X_{bone}$, the auxiliary task of the multi-task neural network is to segment the bone region from the rest of the image. In particular, the loss for the second task regularizes the shape of the bone region by penalizing false classification of other regions as bone. To that end, the second task or the bone mask task is thus driven by the segmentation loss, which may comprise the Dice loss $L_D$ discussed hereinabove:

$$L_{bone}^{seg} = L_D.$$

To generate a bone HU value map or bone HU image $I_{bone}$, the auxiliary task of the multi-task neural network is to generate a continuous density value map within the bone region. Although this third task is a subset of the first task, given that the target dynamic range is large, the loss for the third task regularizes the regression explicitly in the region of interest (e.g., the bone region). To focus on the bone region, the rest of the body regions, along with the background, are considered as the complementary class. The third task or the bone HU image task is thus driven by the regression loss focused on a sub-range of values, defined by:

$$L_{bone}^{reg} = wMAE_{bone}.$$

The overall objective of the multi-task neural network is defined by the composite task of generating a pseudo CT image $I_{pCT}$, a bone map $X_{bone}$, and a bone HU image $I_{bone}$, from an input MR image $I_{MR}$:

$$I_{MR} \rightarrow \{I_{pCT}; X_{bone}; I_{bone}\}.$$

To that end, the multi-task neural network is optimized by minimizing the composite loss function L for the multi-task neural network 320:

$$L = w_1 * L_{body}^{reg} + w_2 * L_{bone}^{seg} + w_3 * L_{bone}^{reg},$$

where the loss coefficient weights $w_1$, $w_2$, and $w_3$ can be either chosen empirically depending on the importance of the corresponding task, or by modeling the uncertainty of each task. As an illustrative example, the loss coefficient weights may be chosen empirically by setting the weight $w_1$ of the primary task to unity, and up-weighting the bone segmentation and regression losses. For example, $w_1$ may be set to 1.0, $w_2$ may be set to 1.5, and $w_3$ may be set to 1.3.

While a single input MR image 310 is depicted in FIG. 3 and described hereinabove, it should be appreciated that in some examples, more than one MR image 310 may be input to the multi-task neural network 320. The input MR image 310 may thus comprise a plurality of MR images 310. For example, the input MR image 310 may comprise a single two-dimensional MR image slice and/or a three-dimensional MR image volume (e.g., comprising a plurality of two-dimensional MR image slices). It should therefore be understood that the term "image" as used herein with regard to an MR image may thus refer to a two-dimensional slice or a three-dimensional volume.

As described further herein with regard to FIG. 4, the multi-task neural network 320 may comprise, as an illustrative and non-limiting example, a two-dimensional U-Net convolutional neural network with multiple output layers. In some illustrative and non-limiting examples, the encoder network may comprise four levels with two blocks of convolution-batch normalization-exponential linear unit (ELU)-max pool operations. These layers may be followed by two blocks of convolutional-batch normalization-ELU operations in a bottleneck layer. The decoder network may comprise four levels with two blocks of upsample-convolution-batch normalization-dropout operations. The input MR image 310 is encoded by blocks of convolutional layers which operate at two different scales (e.g., filter sizes of 7×7 and 5×5) at each resolution. This scale-space feature pyramid at each resolution encodes the features better than a single feature at a single scale. The decoder path is designed with shared layers until the final layer. At the final layer, the pCT image 330 is obtained via a convolution-linear operation, the bone mask 340 is obtained via a convolution-sigmoid operation, and the bone HU value map or bone image 350 is obtained via a convolution-rectified linear unit (ReLU) operation, with each output layer operating with a 1×1 filter size.

As described further herein, the implementation-specific parameters described herein, such as number of filters, U-Net layers, filter size, max-pooling size, and learning rate, are illustrative and non-limiting. Indeed, any suitable neural network configured for multi-task learning may be implemented. One or more specific embodiments of the present disclosure are described herein in order to provide a thorough understanding. The skilled artisan will understand that specific details described in the embodiments can be modified when being placed into practice without deviating the spirit of the present disclosure.

Turning to FIG. 4, architecture for an example multi-task convolutional neural network (CNN) 400 is shown. The multi-task CNN 400, referred to simply and interchangeably as CNN 400 herein, represents one example of a machine learning model according to the current disclosure, wherein the parameters of CNN 400 may be learned using training data produced according to one or more methods disclosed herein. CNN 400 comprises a U-net architecture, which may be divided into an autoencoder portion (descending portion, elements 402-430) and an autodecoder portion (ascending portion, elements 432-458). CNN 400 is configured to receive MR images comprising a plurality of pixels/voxels, and map the input MR image to a plurality of pre-determined types of outputs. CNN 400 includes a series of mappings, from an input image tile 402 which may be received by an input layer, through a plurality of feature maps, and finally to output layers 458a-458c. Although a two-dimensional input is described herein, it should be appreciated that the multi-task neural network(s) described herein, including the multi-task CNN 400, may be configured to additionally or alternatively accept three-dimensional images as input(s). In other words, the multi-task CNN 400 may accept as input two-dimensional MR image slices and/or three-dimensional MR image volumes.

The various elements comprising CNN 400 are labeled in legend 460. As indicated by legend 460, CNN 400 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, and depth, wherein the dimensions refer to the number of neurons comprising the feature map (e.g., how many neurons long, how many neurons wide, and how many neurons deep, a specified feature map is).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 460. Rightward pointing solid black arrows indicate 3×3 convolutions with stride of one, wherein output from a 3×3 grid of feature channels of an immediately preceding feature map are mapped to a single feature channel of a current feature map. Each 3×3 convolution may be followed by an activation function, wherein, in one embodiment, the activation function comprises a rectified linear unit (ReLU).

Downward pointing hollow arrows indicate 2×2 max pooling, wherein the max value from a 2×2 grid of feature channels is propagated from an immediately preceding feature map to a single feature channel of a current feature map, thereby resulting in a 4-fold reduction in spatial resolution of the immediately preceding feature map.

Upward pointing hollow arrows indicate 2×2 up-convolutions, which comprise mapping output from a single feature channel of an immediately preceding feature map to a 2×2 grid of feature channels in a current feature map, thereby increasing the spatial resolution of the immediately preceding feature map 4-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map are equal, no cropping may be performed.

Rightward pointing arrows with hollow elongated triangular heads indicate a 1×1 convolution, in which each feature channel in an immediately preceding feature map is mapped to a single feature channel of a current feature map, or in other words, wherein a 1-to-1 mapping of feature channels between an immediately preceding feature map and a current feature map occurs. Other rightward pointing arrows with hollow triangular heads, as depicted, indicate convolutions with different activation functions, including a linear activation function, a rectified linear unit (ReLU) activation function, and a sigmoid activation function.

In addition to the operations indicated by the arrows within legend 460, CNN 400 includes feature maps that are represented in FIG. 4 by solid filled rectangles, wherein feature maps comprise a height (top to bottom length as shown in FIG. 4, which corresponds to a y spatial dimension in an x-y plane), width (not shown in FIG. 4, assumed equal in magnitude to height, and corresponds to an x spatial dimension in an x-y plane), and depth (a left-right length as shown in FIG. 4, which corresponds to the number of features within each feature channel). Likewise, CNN 400 includes copied and cropped feature maps that are represented in FIG. 4 by hollow (unfilled) rectangles, wherein copied feature maps comprise height (top to bottom length as shown in FIG. 4, which corresponds to a y spatial dimension in an x-y plane), width (not shown in FIG. 4, assumed equal in magnitude to height, and corresponds to an x spatial dimension in an x-y plane), and depth (a length from a left side to a right side as shown in FIG. 4, which corresponds to the number of features within each feature channel).

Starting at input image tile 402 (herein also referred to as an input layer), data corresponding to an MR image may be input and mapped to a first set of features. In some embodiments, the input data is pre-processed (e.g., normalized) before being processed by the neural network. The weights/parameters of each layer of CNN 400 may be learned during a training process, wherein matched pairs of input and expected output (ground truth output) are fed to CNN 400. Parameters may be adjusted based on a gradient descent algorithm, or other algorithm, until the output of CNN 400 matches the expected output (the ground truth output) within a threshold degree of accuracy.

As indicated by the solid black rightward pointing arrow immediately to the right of input image tile 402, a 3×3 convolution of the feature channels of input image tile 402 is performed to produce feature map 404. As discussed above, a 3×3 convolution includes mapping input from a 3×3 grid of feature channels to a single feature channel of a current feature map, using learned weights, wherein the learned weights are referred to as a convolution filter. Each 3×3 convolution in CNN architecture 400 may include a subsequent activation function, which in one embodiment includes passing the output of each 3×3 convolution through a ReLU. In some embodiments, activation functions other than ReLUs may be employed, such as Softplus (also referred to as SmoothReLUs), leaky ReLUs, noisy ReLUs, exponential linear units (ELUs), Tan h, Gaussian, Sin c, Bent identity, logistic functions, and other activation functions known in the art of machine learning.

As indicated by the solid black rightward pointing arrow immediately to the right of feature map 404, a 3×3 convolution is performed on feature map 404 to produce feature map 406.

As indicated by the downward pointing arrow beneath feature map 406, a 2×2 max pooling operation is performed on feature map 406 to produce feature map 408. Briefly, a 2×2 max pooling operation includes determining a max feature value from a 2×2 grid of feature channels of an immediately preceding feature map, and setting a single feature, in a single feature channel, of a current feature map to the max value so determined. Additionally, feature map 406 is copied and concatenated with output from feature map 448 to produce feature map 450, as indicated by the dash-tailed rightward pointing arrow immediately to the right of feature map 406.

As indicated by the solid black rightward pointing arrow immediately to the right of feature map 408, a 3×3 convolution with stride 1 is performed on feature map 408 to produce feature map 410. As indicated by the solid black rightward pointing arrow immediately to the right of feature map 410, a 3×3 convolution with stride 1 is performed on feature map 410 to produce feature map 412.

As indicated by the downward pointing hollow headed arrow beneath feature map 412, a 2×2 max pooling operation is performed on feature map 412 to produce feature map 414, wherein feature map 414 is of one fourth the spatial resolution of feature map 412. Additionally, feature map 412 is copied and concatenated with output from feature map 442 to produce feature map 444, as indicated by the dash-tailed rightward pointing arrow immediately to the right of feature map 412.

As indicated by the solid black rightward pointing arrow immediately to the right of feature map 414, a 3×3 convolution with stride 1 is performed on feature map 414 to produce feature map 416. As indicated by the solid black rightward pointing arrow immediately to the right of feature map 316, a 3×3 convolution with stride 1 is performed on feature map 416 to produce feature map 418.

As indicated by the downward pointing arrow beneath feature map 418, a 2×2 max pooling operation is performed on feature map 418 to produce feature map 420, wherein feature map 420 is of half the spatial resolution of feature map 419. Additionally, feature map 418 is copied and concatenated with output from feature map 436 to produce feature map 438, as indicated by the dash-tailed rightward pointing arrow immediately to the right of feature map 418.

As indicated by the solid black rightward pointing arrow immediately to the right of feature map 420, a 3×3 convolution with stride 1 is performed on feature map 420 to produce feature map 422. As indicated by the solid black rightward pointing arrow immediately to the right of feature map 422, a 3×3 convolution with stride 1 is performed on feature map 422 to produce feature map 424.

As indicated by the downward pointing arrow beneath feature map 424, a 2×2 max pooling operation is performed on feature map 424 to produce feature map 426, wherein feature map 426 is of one fourth the spatial resolution of feature map 424. Additionally, feature map 424 is copied and concatenated with output from feature map 430 to produce feature map 432, as indicated by the dash-tailed rightward pointing arrow immediately to the right of feature map 424.

As indicated by the solid black rightward pointing arrow immediately to the right of feature map 426, a 3×3 convolution is performed on feature map 426 to produce feature map 428. As indicated by the solid black rightward pointing arrow immediately to the right of feature map 428, a 3×3 convolution with stride 1 is performed on feature map 428 to produce feature map 430.

As indicated by the upward pointing arrow immediately above feature map 430, a 2×2 up-convolution is performed on feature map 430 to produce a first half of feature map 432, while copied features from feature map 424 are used to produce a second half of feature map 432. Briefly, a 2×2 up-convolution (herein also referred to as a deconvolution, or up-sampling) with stride of 2, includes mapping a single feature in a single feature channel of an immediately preceding feature map to four features distributed amongst four feature channels in a current feature map (that is, output from a single feature channel is taken as input by four feature channels). Up-convolution/deconvolution/up-sampling comprises projecting a feature value, from a single feature channel, through a deconvolution filter (also herein referred to as a deconvolution kernel) to produce a plurality of outputs.

As indicated by the solid black rightward pointing arrow immediately to the right of feature map 432, a 3×3 convolution is performed on feature map 432 to produce feature map 434.

As indicated in FIG. 4, a 3×3 convolution is performed on feature map 434 to produce feature map 436 and a 2×2 up convolution is performed on feature map 436 to produce half of feature map 438, while copied features from feature map 418 produce the second half of feature map 438. Further, a 3×3 convolution is performed on feature map 438 to produce feature map 440, a 3×3 convolution is performed on feature map 440 to produce feature map 442, and a 2×2 up convolution is performed on feature map 442 to produce a first half of feature map 444, while copied and cropped features from feature map 412 are used to produce the second half of feature map 444. A 3×3 convolution is performed on feature map 444 to produce feature map 446, a 3×3 convolution is performed on feature map 446 to produce feature map 348, and a 2×2 up convolution is performed on feature map 448 to produce a first half of feature map 450, while copied features from feature map 406 are used to produce the second half of feature map 450. A 3×3 convolution is performed on feature map 450 to produce feature map 452, a 3×3 convolution is performed on feature map 452 to produce feature map 454, a 1×1 convolution is performed on feature map 454 to produce output layer 456. Briefly, a 1×1 convolution includes a 1-to-1 mapping of feature channels in a first feature space to feature channels in a second feature space, wherein no reduction in spatial resolution occurs.

As depicted by the multiple arrows pointing away from the output layer 456, multiple outputs may be obtained from the output layer 456 by performing two-dimensional convolutions with different activation functions. First, a two-dimensional convolution with a linear activation function is performed on the output layer 456 to produce a pseudo CT image output 458a. Second, a two-dimensional convolution with a sigmoid activation function is performed on the output layer 456 to produce a bone mask output 458b. Third, a two-dimensional convolution with a ReLU activation function is performed on the output layer 456 to produce a bone image output 458c.

The pseudo CT image output layer 458a comprises an output layer of neurons wherein the output of each neuron corresponds to a pixel of a pseudo CT image. The bone mask output layer 458b comprises an output layer of neurons wherein the output of each neuron corresponds to a pixel of a bone mask or bone mask image. The bone HU image output layer 458c comprises an output layer of neurons wherein the output of each neuron corresponds to a pixel comprising an HU value within a bone region and empty outside of a bone region.

In this way, the multi-task CNN 400 may enable mapping of an MR image to multiple outputs. The architecture of CNN 400 illustrated in FIG. 4 includes the feature map transformations which occur as an input image tile is propagated through the neuron layers of the convolutional neural network, to produce a plurality of predicted outputs.

The weights (and biases) of the convolutional layers in CNN 400 are learned during training, as will be discussed in more detail with reference to FIG. 5 below. Briefly, a loss function is defined to reflect the difference between each predicted output and each ground truth output. A composite difference/loss based on the loss function for each task of the multi-task CNN 400 may be back projected 8 to the CNN 400 to update the weights (and biases) of the convolutional layers. A plurality of training data sets, comprising MR images and corresponding ground truth outputs, may be used to train CNN 400.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 4, or may replace one or more of the shown layers/feature maps.

It should be understood that the architecture and configuration of CNN 400 shown in FIG. 4 is for illustration, not for limitation. Any appropriate multi-task neural network can be used. One or more specific embodiments of the present disclosure are described above in order to provide a thorough understanding. The skilled artisan will understand that specific details described in the embodiments can be modified when being placed into practice without deviating the spirit of the present disclosure.

Figure 5:
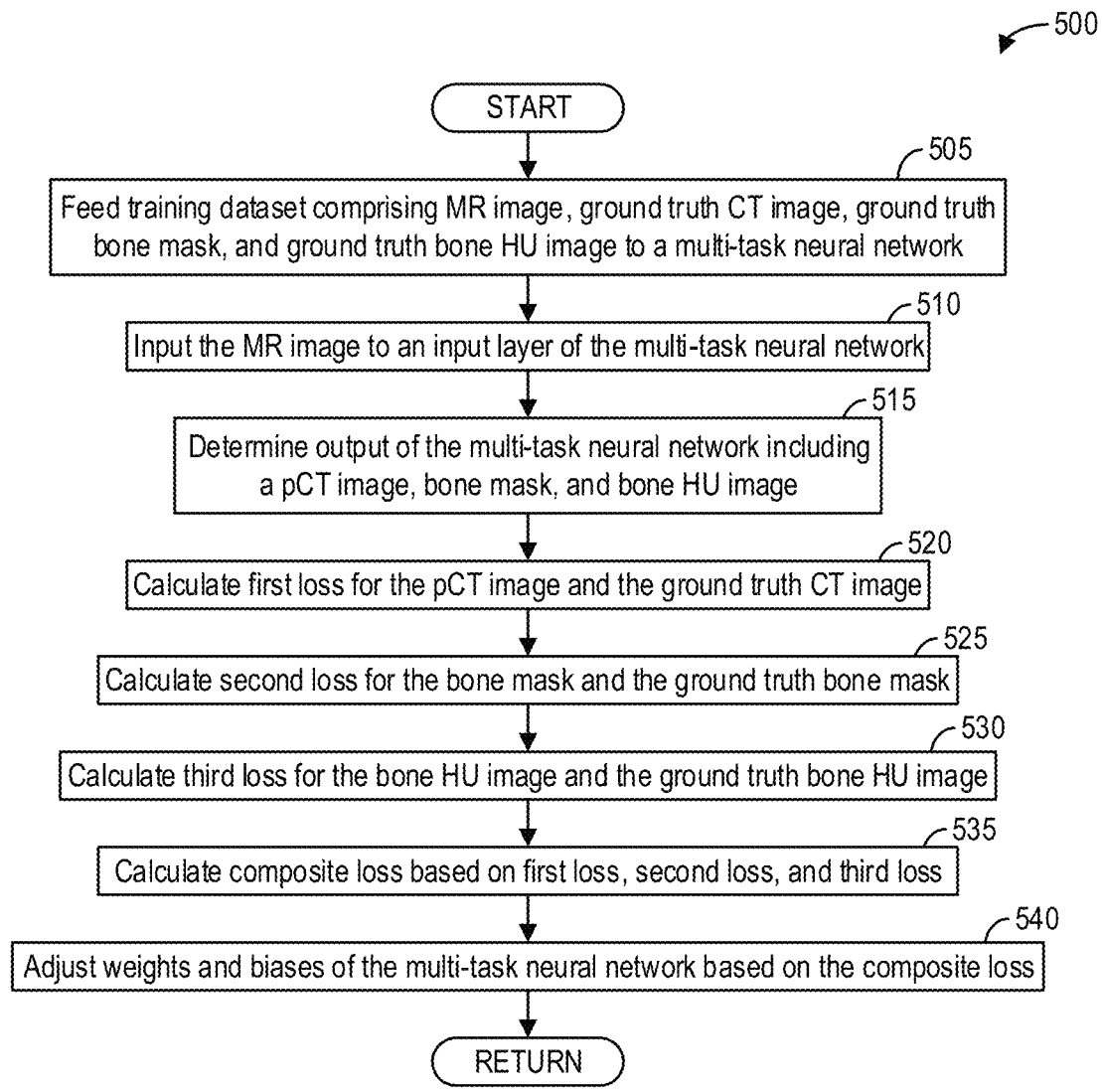
FIG. 5 is a high-level flow chart illustrating an example method for training a deep multi-task neural network to generate pseudo CT images from MR images with a focused region of interest accuracy, according to an embodiment of the disclosure.

FIG. 5 is a high-level flow chart illustrating an example method 500 for training a deep multi-task neural network, such as the CNN 400 shown in FIG. 4, to generate pseudo CT images from MR images with a focused region of interest accuracy, according to an embodiment of the disclosure. Method 500 may be implemented by training module 210.

Method 500 begins at 505. At 505, method 500 feeds a training data set comprising an MR image, a ground truth CT image, a ground truth bone mask, and a ground truth bone HU image to a multi-task neural network. The MR image and the ground truth CT image comprise medical images of a same region of interest of a same patient acquired via MR and CT imaging modalities, respectively, such that the MR image and the ground truth CT image correspond to each other. The ground truth bone mask and the ground truth bone HU image are generated from the ground truth CT image. For example, the ground truth CT image may be segmented to obtain segments of the ground truth CT image containing bone, and the ground truth bone mask may comprise the segments of the ground truth CT image containing bone. The ground truth bone mask thus comprises an image mask indicating the positions of the ground truth CT image corresponding to bone and further indicating positions of the ground truth CT image not corresponding to bone, for example, by representing the bone segments as black pixels and the non-bone segments as white pixels, or vice versa. Similarly, whereas the ground truth bone mask comprises an image mask indicating the bone segments, the ground truth bone HU value map or ground truth bone HU image comprises the HU values within the bone segments.

A ground truth may include an expected, ideal, or "correct" result from the multi-task neural network based on input of the MR image. The ground truth outputs including the ground truth CT image, the ground truth bone mask, and the ground truth bone HU image correspond to the MR image so that the multi-task neural network described herein may be trained on multiple tasks, including generating a pseudo CT image corresponding to the MR image, generating a bone mask indicating positions of bone within the pseudo CT image, and generating a bone HU image indicating bone HU values within the pseudo CT image. The training data set, and a plurality of training data sets including the training data set, may be stored in the image processing system, such as in the medical image data 212 of the image processing system 202.

At 510, method 500 inputs the MR image to an input layer of the multi-task neural network. For example, the MR image is input to the input layer 402 of the multi-task CNN 400. In some examples, each voxel or pixel value of the MR image is input to a distinct node/neuron of the input layer of the multi-task neural network.

At 515, method 500 determines current output of the multi-task neural network including a pCT image, a bone mask, and a bone HU image. For example, the multi-task neural network maps the input MR image to the pCT image, the bone mask, and the bone HU image by propagating the input MR image from the input layer, through one or more hidden layers, until reaching an output layer of the multi-task neural network. The pCT image, the bone mask, and the bone HU image comprise the output of the multi-task neural network.

At 520, method 500 calculates a first loss for the pCT image and the ground truth CT image. Method 500 may calculate the first loss by calculating the difference between the pCT image output by the multi-task neural network and the ground truth CT image. For example, as the first task of the multi-task neural network is the whole image regression of the entire CT value (HU) range corresponding to different classes, the first loss $L_{body}^{reg}$ may be calculated according to:

$$L_{body}^{reg} = MAE_{body},$$

where $MAE_{body}$ comprises the mean absolute error for the entire body region including bone region(s), tissue region(s), and so on, as described hereinabove with regard to FIG. 3.

At 525, method 500 calculates a second loss for the bone mask and the ground truth bone mask. Method 500 may calculate the second loss by calculating the difference between the bone mask output by the multi-task neural network and the ground truth bone mask. For example, as the second task of the multi-task neural network is to segment the bone regions of the MR image, the second loss regularizes the shape of the bone region by penalizing false classification of other regions as bone. To that end, the second loss $L_{bone}^{seg}$ may be calculated as:

$$L_{bone}^{seg} = L_D,$$

wherein the Dice loss $L_D$ may comprise a smoothed Dice coefficient loss as described hereinabove with regard to FIG. 3.

At 530, method 500 calculates a third loss for the bone HU image and the ground truth bone HU image. Method 500 may calculate the third loss by calculating the difference between the bone HU image output by the multi-task neural network and the ground truth bone HU image. For example, the third loss regularizes the regression explicitly in the region of interest (e.g., the bone region), and to focus on the bone region, the rest of the body regions, along with the background, are considered as the complementary class. Method 500 may thus calculate the third loss by calculating a regression loss focused on a sub-range of values, defined by:

$$L_{bone}^{reg} = wMAE_{bone},$$

wherein wMAE$_{bone}$ comprises the weighted mean absolute error for the bone region as described hereinabove with regard to FIG. 3.

At 535, method 500 calculates a composite loss based on the first loss, the second loss, and the third loss. For example, method 500 calculates the composite loss function L for the multi-task neural network:

$$L = w_1 * L_{body}^{reg} + w_2 * L_{bone}^{seg} + w_3 * L_{bone}^{reg},$$

wherein the loss coefficient weights $w_1$, $w_2$, and $w_3$ may be determined based on the importance of the corresponding task, or by modeling the uncertainty of each task.

At 540, method 500 adjusts weights and biases of the multi-task neural network based on the composite loss calculated at 535. The composite loss may be back propagated through the multi-task neural network to update the weights and biases of the convolutional layers. In some examples, back propagation of the composite loss may occur according to a gradient descent algorithm, wherein a gradient of the composite loss function (a first derivative, or approximation of the first derivative) is determined for each weight and bias of the multi-task neural network. Each weight and bias is then updated by adding the negative of the product of the gradient determined (or approximated) for the weight or bias with a predetermined step size. Method 500 then returns. It should be appreciated that method 500 may be repeated until the weights and biases of the multi-task neural network converge, or the rate of change of the weights and/or biases of the multi-task neural network for each iteration of method 500 are under a threshold.

In this way, method 500 enables a multi-task neural network to be trained to generate a pseudo CT image with increased structural and quantitative accuracy in regions with varying electron densities, with a particular focus on accurate bone value prediction.

Figure 6:
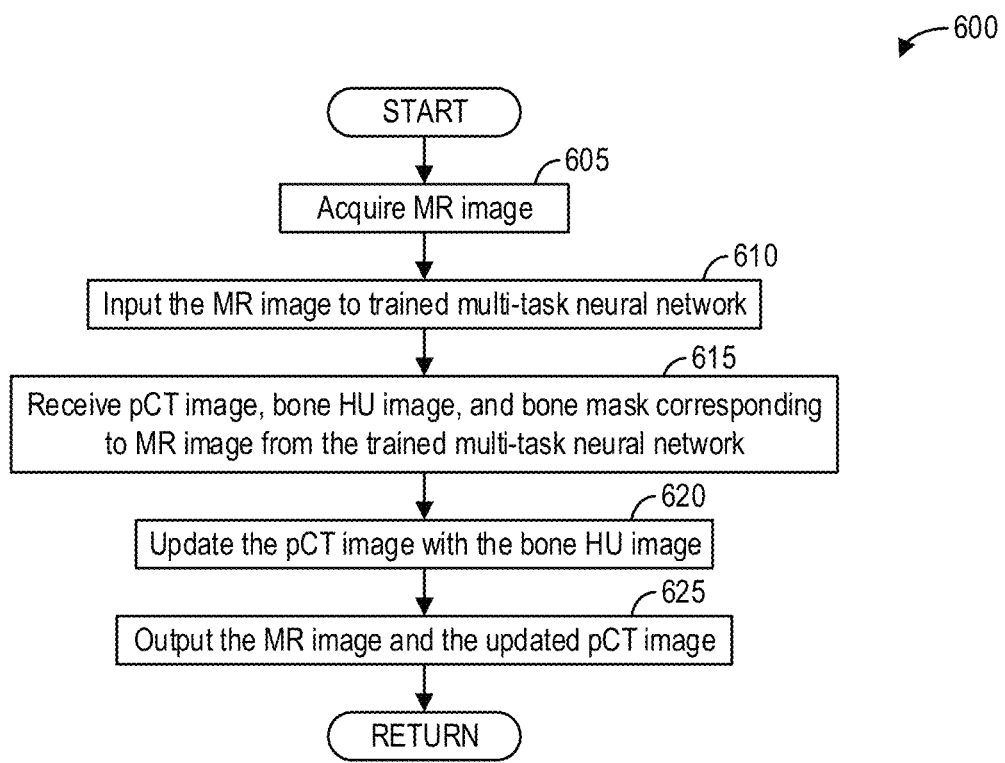
FIG. 6 is a high-level flow chart illustrating an example method for generating pseudo CT images from MR images with a deep multi-task neural network, according to an embodiment of the disclosure.

Once the multi-task neural network is trained as described hereinabove, the multi-task neural network may be deployed for use in generating pseudo CT images, which in turn may be used for improving clinical workflows with a single imaging modality. As an illustrative example, FIG. 6 is a high-level flow chart illustrating an example method 600 for generating pseudo CT images from MR images with a deep multi-task neural network, according to an embodiment of the disclosure. Method 600 is described with regard to the systems and components of FIGS. 1-4, though it should be appreciated that the method 600 may be implemented with other systems and components without departing from the scope of the present disclosure. Method 600 may be implemented as executable instructions in non-transitory memory 206 that are executable by the processor 204 of an image processing system 202, for example, which may be integrated into an imaging system such as the MIl apparatus 10.

Method 600 begins at 605. At 605, method 600 acquires an MR image. In examples wherein the medical image processing system 200 is integrated into an imaging system such as the MRI apparatus 10, for example, method 600 may control the MM apparatus 10 to perform a scan of a subject, such as a patient, by generating RF signals and measuring MR signals. In such examples, method 600 may further construct an MR image of the subject from the measured MR signals as described hereinabove with regard to FIG. 1. In other examples, wherein the image processing system 200 is disposed at a separate device (e.g., a workstation) communicatively coupled to an imaging system such as the MRI apparatus 10 and configured to receive MR images from the imaging system, method 600 may acquire the MR image by retrieving or receiving the MR image from the imaging system. In yet other examples, method 600 may acquire the MR image by retrieving the MR image from storage, for example via a picture archiving and communication system (PACS).

At 610, method 600 inputs the MR image to the trained multi-task neural network. In some examples, the trained multi-task neural network comprises a U-Net two-dimensional convolutional neural network architecture configured with multiple output layers, such as the CNN 400 described hereinabove with regard to FIG. 4 having an autoencoder-autodecoder type architecture, trained according to the training method 500 described hereinabove with regard to FIG. 5. The trained multi-task neural network generates, based on the input MR image, at least a pseudo CT (pCT) image corresponding to the MR image, as well as additional outputs related to other tasks, such as a bone mask and a bone HU image as described hereinabove.

Thus, at 615, method 600 receives a pCT image, a bone HU image, and a bone mask corresponding to the MR image from the trained multi-task neural network. As the bone HU image is generated with the specific objective of quantitative accuracy, the HU values of the bone region indicated by the bone mask are potentially more accurate than the HU values of the same region in the pCT image. Therefore, at 620, method 600 updates the pCT image with the bone HU image. For example, method 600 may paste the bone HU image onto the pCT image, guided by the bone mask in some examples, such that the bone HU values depicted in the bone HU image replace the corresponding pixels in the pCT image. Alternatively, the bone HU image may be blended with the pCT image to improve the quantitative accuracy of the pCT image without replacing the pixels of the pCT image.

At 620, method 600 outputs the MR image and the updated pCT image. For example, method 600 may display the MR image and the updated pCT image via a display device, such as display device 214 or display unit 33. Method 600 then returns.

Figure 7:
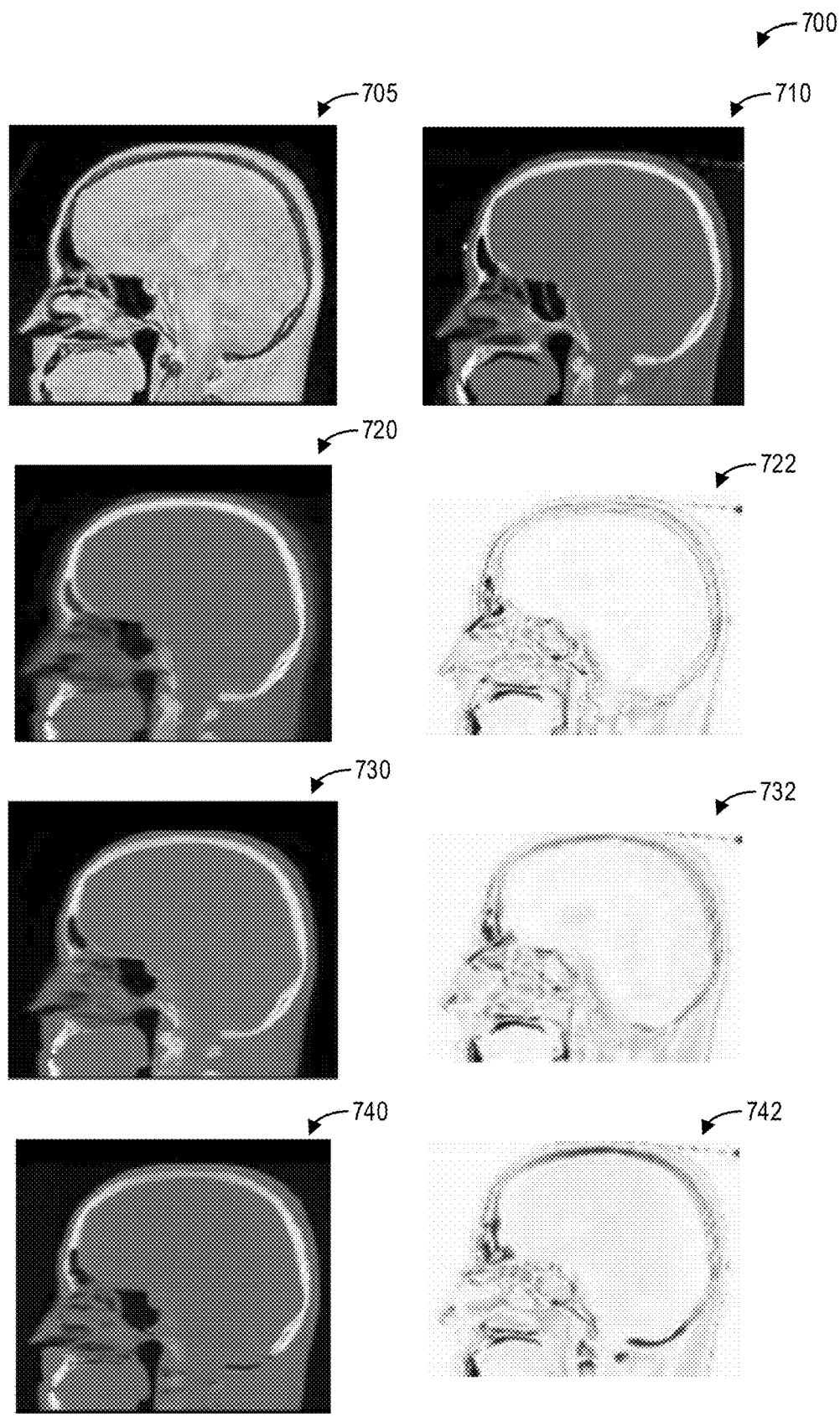
FIG. 7 shows a set of images illustrating example pseudo CT images generated according to different techniques compared to an input MR image and a ground truth CT image.

FIG. 7 shows a set of images 700 illustrating example pseudo CT images generated according to different techniques compared to an input MR image 705 and a ground truth CT image 710. The input MR image 705 comprises a zero echo time (ZTE) MR image of a patient acquired by controlling an MR apparatus during an MR scan with a ZTE protocol adapted to capture bone information in a single contrast MRI. The ground truth CT image 710 comprises a CT image of a patient acquired by controlling a CT imaging system to perform a CT scan of the patient.

Image registration between the MR image 705 and the ground truth CT image 710 is also performed. For example, the CT image 710 is aligned to match the MR image space of the MR image 705 by applying an affine transformation to the CT image. As an illustrative example, the registration may be performed by minimizing a combination of mutual-information and cross-correlation metrics. Such registration may be performed in particular for MR-CT image training pairs, to further improve the accuracy of pCT image regression, bone segmentation, and bone image regression from an MR image performed by the multi-task neural network described herein.

As mentioned hereinabove, the set of images 700 further includes example pseudo CT images generated according to different techniques. For example, the first pseudo CT image 720 comprises a multi-task pseudo CT image 720 generated from the input MR image 705 with a multi-task neural network as described hereinabove. The difference map 722 depicts the pixel-wise difference or residual error (e.g., $I_{CT}-I_{pCT}$) between the ground truth CT image 710 and the multi-task pseudo CT image 720.

Further, the second pseudo CT image 730 comprises a single-task pseudo CT image 730 generated from the input MR image 705 with a single-task neural network adapted with a similar architecture as the multi-task neural network described herein but trained for only the single task of pseudo CT image regression. The difference map 732 depicts the difference between the ground truth CT image 710 and the single-task pseudo CT image 730.

As another example, the third pseudo CT image 740 comprises a standard pseudo CT image 740 generated from the input MR image 705 with a standard regression network, in particular a fully-connected DenseNet56 neural network trained to perform pseudo CT image regression. The difference map 742 depicts the difference between the ground truth CT image 710 and the standard pseudo CT image 740.

As depicted, the residual error depicted by the difference map 722 for the multi-task pseudo CT image 720 is lower than the residual error depicted by the difference maps 732 and 742. The multi-task pseudo CT image 720 and the single-task pseudo CT image 730 look similar, but a comparison of the difference maps 722 and 732 indicates a lower error for the multi-task pseudo CT image 720 throughout the bone regions of the image, in particular the frontal bone and nasal bone regions of the skull, as depicted by the darker regions in the difference map 732. The difference map 742 indicates more extensive residual error throughout the bone regions, such as in the occipital bone region of the skull.

Figure 8:
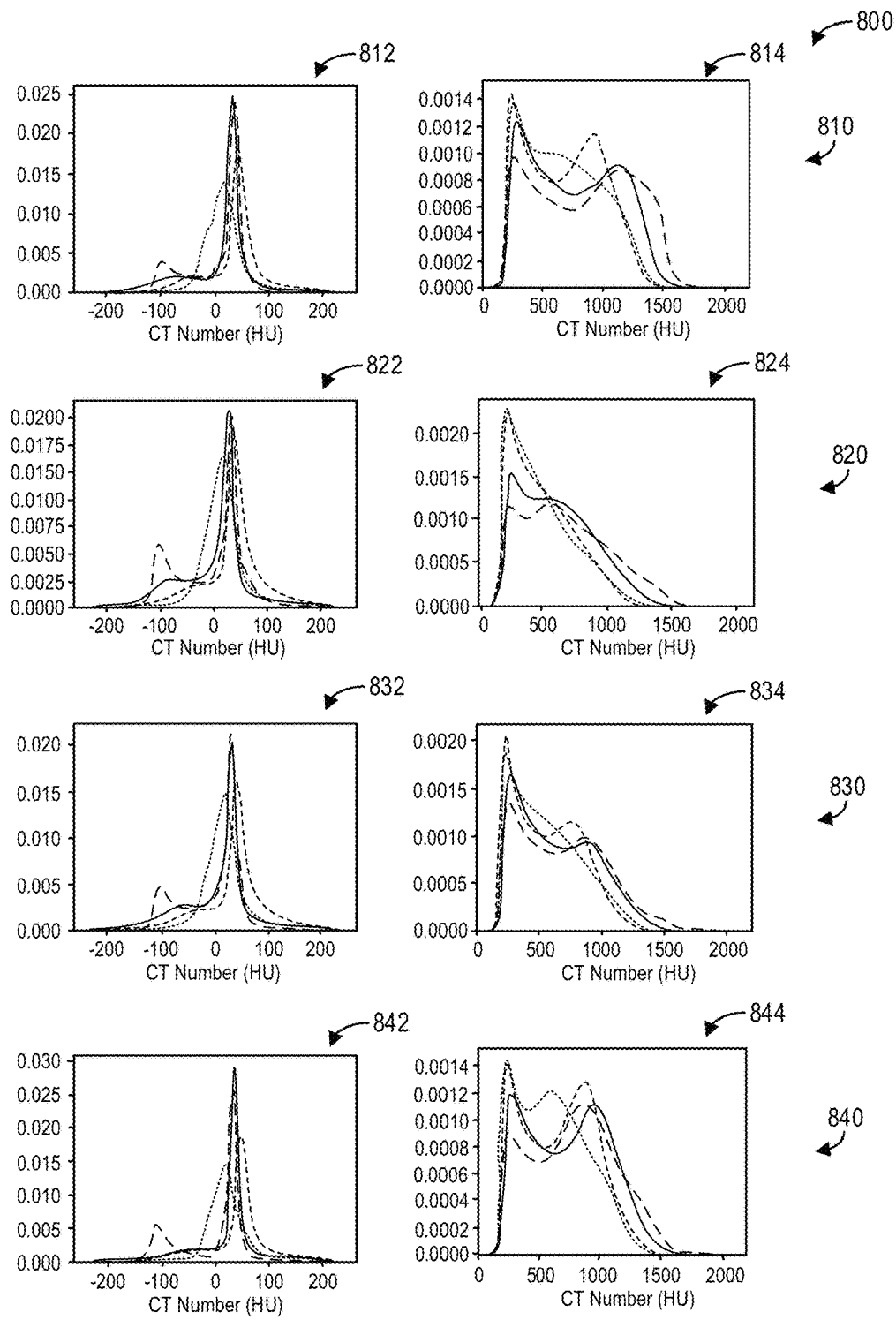
FIG. 8 shows a set of graphs illustrating normalized histograms of soft-tissue and bone regions of pseudo CT and CT images for a plurality of cases.

As another illustrative example of the qualitative differences between the multi-task neural network provided herein and the use of standard, single-task neural networks, FIG. 8 shows a set of graphs 800 illustrating normalized histograms of soft-tissue and bone regions of pseudo CT and CT images for a plurality of cases. In particular, the set of graphs 800 includes: a first set of graphs 810 for a first case, including a graph 812 of soft-tissue regions and a graph 814 of bone regions; a set of graphs 820 for a second case, including a graph 822 of soft-tissue regions and a graph 824 of bone regions; a set of graphs 830 for a third case, including a graph 832 of soft-tissue regions and a graph 834 of bone regions; and a fourth set of graphs 840 for a fourth case, including a graph 842 of soft-tissue regions and a graph 844 of bone regions.

Each graph illustrates plots of normalized histograms for a ground truth CT image as well as pseudo CT images acquired via the various techniques described hereinabove, including the multi-task neural network described herein, a single-task neural network, and a standard DenseNet neural network. In particular, as depicted by the legend 880, plots with a solid line correspond to measurements for the multi-task neural network, plots with the longer dashed lines correspond to measurements for the ground truth CT image, plots with the short dashed lines correspond to measurements for the single-task neural network, and plots with the shortest dashed lines correspond to measurements for the DenseNet56 neural network.

The closeness of the predicted image histogram with the CT histogram in each region is an indicator of image similarity at different values in the range. As depicted in each graph of the set of graphs 800, the pseudo CT histogram for the multi-task neural network (depicted by the solid plots) more closely matches the ground truth CT histogram (depicted by the longer dash plots) relative to the other pseudo CT histograms (depicted by the shorter dash plots) for both soft-tissue regions and bone regions, across all HU values.

The qualitative analysis depicted in FIGS. 7 and 8 indicates that the multi-task neural network described herein provides a substantial qualitative improvement over other neural network-based approaches to pseudo CT image regression. Further, a quantitative analysis of the different techniques also confirms that a multi-task neural network configured and trained as described herein for pseudo CT image regression achieves better performance relative to other approaches. For example, for the proposed multi-task neural network evaluated with five cases, the mean absolute error (MAE) in the body region $MAE_{body}$ is 90.21±8.06, the MAE in the soft-tissue region $MAE_{soft-tissue}$ is 61.60±7.20, and the MAE in the bone region $MAE_{bone}$ is 159.38±12.48. In contrast, for the single-task neural network evaluated with the same five cases, the MAE in the body region $MAE_{body}$ is 103.05±10.55, the MAE in the soft-tissue region $MAE_{soft-tissue}$ is 66.90±8.24, and the MAE in the bone region $MAE_{bone}$ is 214.50±16.05. Similarly, for the DenseNet56 neural network evaluated with the same five cases, the MAE in the body region $MAE_{body}$ is 109.92±12.56, the MAE in the soft-tissue region $MAE_{soft-tissue}$ is 64.88±8.36, and the MAE in the bone region $MAE_{bone}$ is 273.66±24.88. The MAE in the body $MAE_{body}$ is an indication of overall accuracy of prediction. MAE in the soft-tissue region $MAE_{soft-tissue}$, which ranges from −200 HU to 250 HU, indicates the accuracy of prediction in low density values. MAE in the bone region $MAE_{bone}$, which ranges from 250 HU to 3000 HU, indicates the accuracy of prediction in the bone value range. The particular advantage of the multi-task neural network over other networks is thus readily apparent in the bone region error. The reduced error for the multi-task neural network may be attributed to the advantage of ROI-focused losses, via the additional tasks of bone segmentation and bone image regression, driving the image regression in the bone region.

Figure 9:
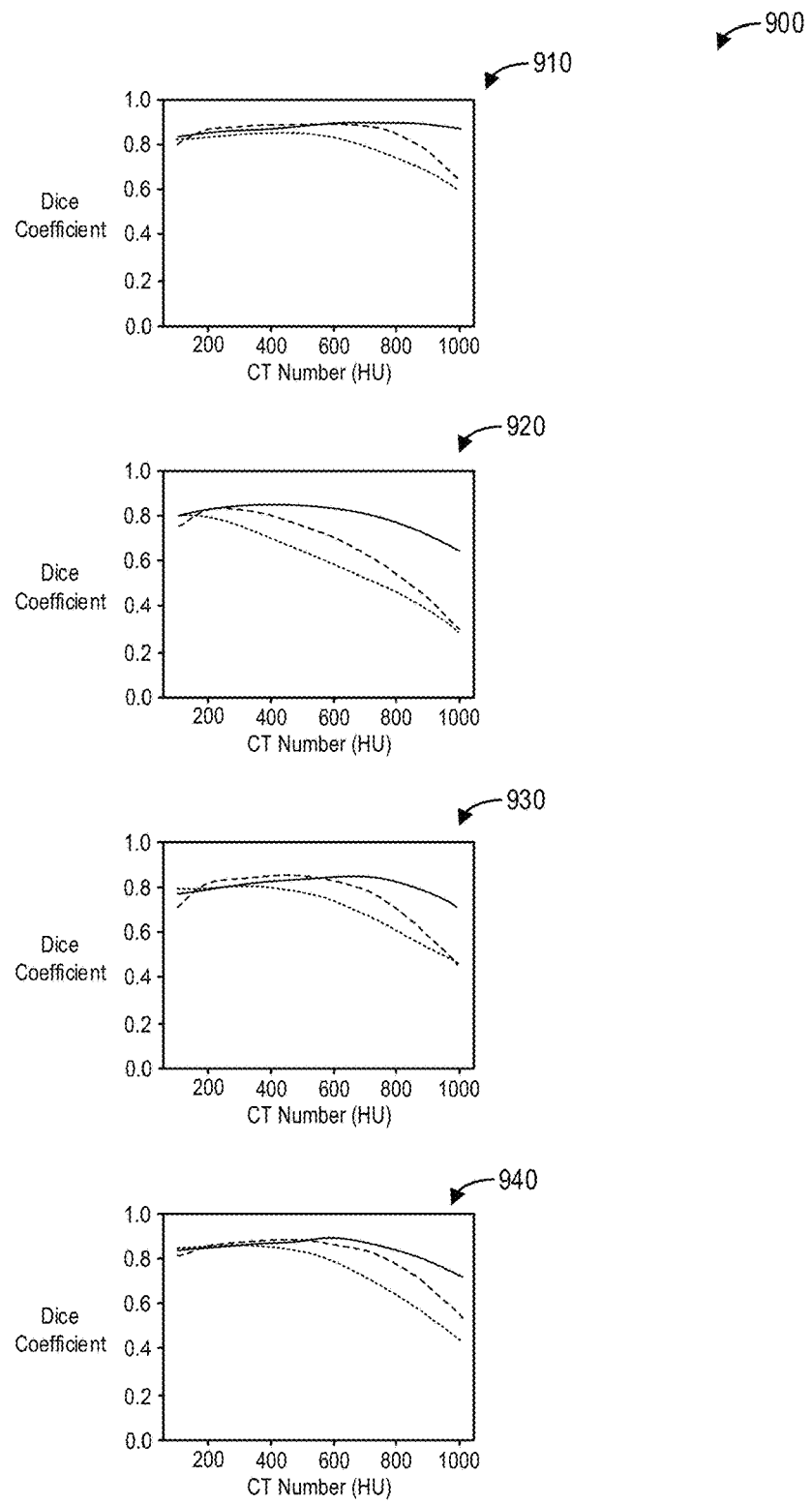
FIG. 9 shows a set of graphs illustrating plots of Dice coefficients for pseudo CT bone regions at different bone density thresholds for a plurality of cases.

Further, as an additional illustrative example, FIG. 9 shows a set of graphs 900 illustrating plots of Dice coefficients for pseudo CT bone regions at different bone density thresholds for a plurality of cases. The set of graphs 900 includes a graph 910 for a first case, a graph 920 for a second case, a graph 930 for a third case, and a graph 940 for a fourth case, wherein each graph depicts a plot for the multi-task neural network (the solid lines), a plot for the single-task neural network (the longer dash lines), and a plot for the DenseNet56 neural network (the shorter dash lines), as indicated by the legend 980. The deteriorating of the curve at higher CT numbers or HU values indicates an underestimation of high density bone values. While the multi-task neural network exhibits a slight deterioration for high density bone values, the single-task neural network and the DenseNet56 exhibit substantially worse estimation for the same bone values. Thus, in comparison to standard neural network approaches to pCT image regression, the multi-task neural network proposed and described herein with enhanced focus on bone ensures an accurate prediction across all HU values.

In order to evaluate the utility of the multi-task neural network in radiation therapy treatment planning, a comparative analysis of the pCT dosimetric performance in radiation therapy treatment planning was performed. After collecting MR and CT data for two patients with brain tumors, treatment plans were developed based on the CT images using standard clinical guidelines and with ROIs drawn by physicians. The treatment plans were then evaluated based on both CT and pCT data (generated by the multi-task neural network described herein) with a treatment planning system, and the results were compared. The difference in average dose to the Planning Target Volume (PTV) relative to the prescribed dose was found to be 0.18% and −0.13%, respectively. Thus, the use of the multi-task neural network to generate accurate pseudo CT images from MR images enables the replacement of CT imaging for obtaining density maps for radiation therapy dose calculations, and thus enables MR-only clinical workflows for radiation therapy.

The technical effect of the present disclosure includes the generation of a pseudo CT image from an MR image. Another technical effect of the present disclosure includes the generation of a CT-like image from an MR image with enhanced accuracy in regions containing bone. Yet another technical effect of the present disclosure includes the generation of a pseudo CT image, a bone mask, and a bone image with a multi-task neural network based on an input MR image.

In one embodiment, a method comprises acquiring a magnetic resonance (MR) image, generating, with a multi-task neural network, a pseudo CT image corresponding to the MR image, and outputting the MR image and the pseudo CT image.

In a first example of the method, the multi-task neural network is trained with a focused loss for a region of interest including bone in the MR image. In a second example of the method optionally including the first example, the method further comprises generating, with the multi-task neural network, a bone mask and a bone image corresponding to the MR image. In a third example of the method optionally including one or more of the first and second examples, the multi-task neural network is trained with a whole image regression loss for the pseudo CT image, a segmentation loss for the bone mask, and a regression loss focused on bone segments for the bone image. In a fourth example of the method optionally including one or more of the first through third examples, the method further comprises training the multi-task neural network with a composite loss comprising the whole image regression loss, the segmentation loss, and the regression loss focused on the bone segments, wherein each loss is weighted in the composite loss. In a fifth example of the method optionally including one or more of the first through fourth examples, the method further comprises updating the pseudo CT image with the bone image, and outputting the updated pseudo CT image with the MR image. In a sixth example of the method optionally including one or more of the first through fifth examples, the multi-task neural network comprises a U-Net convolutional neural network configured with multiple output layers, wherein one output layer of the multiple output layers outputs the pseudo CT image.

In another embodiment, a magnetic resonance imaging (MM) system comprises an MRI scanner, a display device, a controller unit communicatively coupled to the MRI scanner and the display device, and a memory storing executable instructions that when executed cause the controller unit to: acquire, via the MRI scanner, a magnetic resonance (MR) image; generate, with a multi-task neural network, a pseudo CT image corresponding to the MR image; and output, to the display device, the MR image and the pseudo CT image.

In a first example of the MM system, the multi-task neural network is trained with a focused loss for a region of interest including bone in the MR image. In a second example of the MM system optionally including the first example, the memory further stores executable instructions that when executed cause the controller unit to generate, with the multi-task neural network, a bone mask and a bone image corresponding to the MR image. In a third example of the MRI system optionally including one or more of the first and second examples, the multi-task neural network is trained with a whole image regression loss for the pseudo CT image, a segmentation loss for the bone mask, and a regression loss focused on bone segments for the bone image. In a fourth example of the MRI system optionally including one or more of the first through third examples, the memory further stores executable instructions that when executed cause the controller unit to train the multi-task neural network with a composite loss comprising the whole image regression loss, the segmentation loss, and the regression loss focused on the bone segments, wherein each loss is weighted in the composite loss. In a fifth example of the MRI system optionally including one or more of the first through fourth examples, the memory further stores executable instructions that when executed cause the controller unit to update the pseudo CT image with the bone image, and output, to the display device, the updated pseudo CT image with the MR image.

In yet another embodiment, a non-transitory computer-readable medium comprises instructions that, when executed, cause a processor to: acquire a magnetic resonance (MR) image; generate, with a multi-task neural network, a pseudo CT image corresponding to the MR image; and output, to a display device, the MR image and the pseudo CT image.

In a first example of the non-transitory computer-readable medium, the multi-task neural network is trained with a focused loss for a region of interest including bone in the MR image. In a second example of the non-transitory computer-readable medium optionally including the first example, the instructions when executed further cause the processor to generate, with the multi-task neural network, a bone mask and a bone image corresponding to the MR image. In a third example of the non-transitory computer-readable medium optionally including one or more of the first and second examples, the multi-task neural network is trained with a whole image regression loss for the pseudo CT image, a segmentation loss for the bone mask, and a regression loss focused on bone segments for the bone image. In a fourth example of the non-transitory computer-readable medium optionally including one or more of the first through third examples, the instructions when executed further cause the processor to train the multi-task neural network with a composite loss comprising the whole image regression loss, the segmentation loss, and the regression loss focused on the bone segments, wherein each loss is weighted in the composite loss. In a fifth example of the non-transitory computer-readable medium optionally including one or more of the first through fourth examples, the instructions when executed further cause the processor to update the pseudo CT image with the bone image, and output, to the display device, the updated pseudo CT image with the MR image. In a sixth example of the non-transitory computer-readable medium optionally including one or more of the first through fifth examples, the multi-task neural network comprises a U-Net convolutional neural network configured with multiple output layers, wherein one output layer of the multiple output layers outputs the pseudo CT image.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    acquiring a magnetic resonance (MR) image;
    generating, with a multi-task neural network, a pseudo CT image, a bone mask, and a bone Hounsfield unit (HU) image corresponding to the MR image, wherein the pseudo CT image comprises a set of three density classes, the density classes comprising air, tissue, and bone, and wherein the bone HU image includes image values within a bone region of interest in terms of HU; and
    outputting the MR image and the pseudo CT image,
    wherein the multi-task neural network is trained with a whole image regression loss for the pseudo CT image, a segmentation loss for the bone mask, and a regression loss focused on bone segments for the bone HU image.

2. The method of claim 1, wherein the multi-task neural network is trained with a focused loss for a region of interest including bone in the MR image.

3. The method of claim 1, further comprising training the multi-task neural network with a composite loss comprising the whole image regression loss, the segmentation loss, and the regression loss focused on the bone segments, wherein each loss is weighted in the composite loss.

4. The method of claim 1, further comprising updating the pseudo CT image with the bone HU image, and outputting the updated pseudo CT image with the MR image.

5. The method of claim 1, wherein the multi-task neural network comprises a U-Net convolutional neural network configured with multiple output layers, and wherein one output layer of the multiple output layers outputs the pseudo CT image.

6. A magnetic resonance imaging (MRI) system, comprising:
    an MRI scanner;
    a display device;
    a controller unit communicatively coupled to the MRI scanner and the display device; and
    a memory storing executable instructions that when executed cause the controller unit to:
        acquire, via the MRI scanner, a magnetic resonance (MR) image;
        generate, with a multi-task neural network, a pseudo CT image, a bone mask, and a bone Hounsfield unit (HU) image corresponding to the MR image, wherein the pseudo CT image comprises a set of three density classes, the density classes comprising air, tissue, and bone, and wherein the bone HU image includes image values within a bone region of interest in terms of HU; and
        output, to the display device, the MR image and the pseudo CT image,
    wherein the multi-task neural network is trained with a whole image regression loss for the pseudo CT image, a segmentation loss for the bone mask, and a regression loss focused on bone segments for the bone HU image.

7. The MRI system of claim 6, wherein the multi-task neural network is trained with a focused loss for a region of interest including bone in the MR image.

8. The MRI system of claim 6, the memory further storing executable instructions that when executed cause the controller unit to train the multi-task neural network with a composite loss comprising the whole image regression loss, the segmentation loss, and the regression loss focused on the bone segments, wherein each loss is weighted in the composite loss.

9. The MRI system of claim 6, the memory further storing executable instructions that when executed cause the controller unit to update the pseudo CT image with the bone HU image, and output, to the display device, the updated pseudo CT image with the MR image.

10. A non-transitory computer-readable medium comprising instructions that when executed cause a processor to:
    acquire a magnetic resonance (MR) image;
    generate, with a multi-task neural network, a pseudo CT image, a bone mask, and a bone Hounsfield unit (HU) image corresponding to the MR image, wherein the pseudo CT image comprises a set of three density classes, the density classes comprising air, tissue, and bone, and wherein the bone HU image includes image values within a bone region of interest in terms of HU; and
    output, to a display device, the MR image and the pseudo CT image,
    wherein the multi-task neural network is trained with a whole image regression loss for the pseudo CT image, a segmentation loss for the bone mask, and a regression loss focused on bone segments for the bone HU image.

11. The non-transitory computer-readable medium of claim 10, wherein the multi-task neural network is trained with a focused loss for a region of interest including bone in the MR image.

12. The non-transitory computer-readable medium of claim 10, wherein the instructions when executed further cause the processor to train the multi-task neural network with a composite loss comprising the whole image regression loss, the segmentation loss, and the regression loss focused on the bone segments, wherein each loss is weighted in the composite loss.

13. The non-transitory computer-readable medium of claim 10, wherein the instructions when executed further cause the processor to update the pseudo CT image with the bone HU image, and output, to the display device, the updated pseudo CT image with the MR image.

14. The non-transitory computer-readable medium of claim 10, wherein the multi-task neural network comprises a U-Net convolutional neural network configured with multiple output layers, and wherein one output layer of the multiple output layers outputs the pseudo CT image.

15. A method, comprising:
   acquiring a magnetic resonance (MR) image;
   generating, with a multi-task neural network, a pseudo CT image, a bone mask, and a bone image corresponding to the MR image, wherein the pseudo CT image comprises a set of three density classes, the density classes comprising air, tissue, and bone, wherein the bone mask is obtained via a convolution-sigmoid operation, and the bone image is obtained via a convolution-rectified linear unit (ReLU) operation; and
   outputting the MR image and the pseudo CT image.

* * * * *